(12) United States Patent
Renzi et al.

(10) Patent No.: US 8,163,254 B1
(45) Date of Patent: *Apr. 24, 2012

(54) MICROMANIFOLD ASSEMBLY

(75) Inventors: Ronald F. Renzi, Tracy, CA (US); Scott M. Ferko, Livermore, CA (US)

(73) Assignee: Sandia Corporation, Albuquerque, NM (US)

(*) Notice: Subject to any disclaimer, the term of this patent is extended or adjusted under 35 U.S.C. 154(b) by 246 days.

This patent is subject to a terminal disclaimer.

(21) Appl. No.: 12/476,002

(22) Filed: Jun. 1, 2009

Related U.S. Application Data

(62) Division of application No. 10/405,842, filed on Apr. 2, 2003, now Pat. No. 7,553,455.

(51) Int. Cl.
*B01L 3/00* (2006.01)
*B01L 3/02* (2006.01)

(52) U.S. Cl. ........ 422/502; 422/503; 422/504; 422/500; 422/501; 422/512

(58) Field of Classification Search ............ 422/512, 422/500–504
See application file for complete search history.

(56) References Cited

U.S. PATENT DOCUMENTS

| | | | | |
|---|---|---|---|---|
| 5,890,745 A * | 4/1999 | Kovacs | | 285/24 |
| 6,102,449 A * | 8/2000 | Welsh | | 285/342 |
| 6,284,113 B1 * | 9/2001 | Bjornson et al. | | 204/453 |
| 6,319,476 B1 * | 11/2001 | Victor et al. | | 422/502 |
| 6,376,253 B1 * | 4/2002 | Anderson et al. | | 436/86 |
| 6,682,702 B2 * | 1/2004 | Barth et al. | | 422/552 |
| 6,756,019 B1 * | 6/2004 | Dubrow et al. | | 422/502 |
| 6,811,668 B1 * | 11/2004 | Berndt et al. | | 204/601 |
| 6,811,752 B2 * | 11/2004 | Barbera-Guillem | | 422/503 |
| 6,832,787 B1 * | 12/2004 | Renzi | | 285/124.1 |
| 7,311,882 B1 * | 12/2007 | Renzi | | 422/546 |
| 7,452,507 B2 * | 11/2008 | Renzi et al. | | 422/82.05 |
| 7,553,455 B1 * | 6/2009 | Renzi et al. | | 422/546 |
| 2002/0110900 A1 * | 8/2002 | Jovanovich et al. | | 435/286.4 |
| 2002/0172621 A1 * | 11/2002 | Barbera-Guillem | | 422/100 |
| 2004/0126279 A1 * | 7/2004 | Renzi et al. | | 422/100 |

* cited by examiner

*Primary Examiner* — Brian R Gordon

(74) *Attorney, Agent, or Firm* — Timothy R. Evans

(57) ABSTRACT

A micromanifold for connecting external capillaries to the inlet and/or outlet ports of a microfluidic device can employ a ferrule/capillary assembly that includes: (a) a ferrule comprising an elongated member and having a bore traversing from a proximal end to a distal end of the member, wherein the bore has an inner surface and wherein the distal end of the ferrule has a tapered, threaded exterior surface, and (b) a capillary that is positioned within the bore wherein the capillary's outer surface is in direct contact with the bore's inner surface. No mating sleeve is required for the one-piece ferrule. Alternatively, the capillaries can be bonded to channels that traverse the manifold and therefore obviate the need for a ferrule.

8 Claims, 3 Drawing Sheets

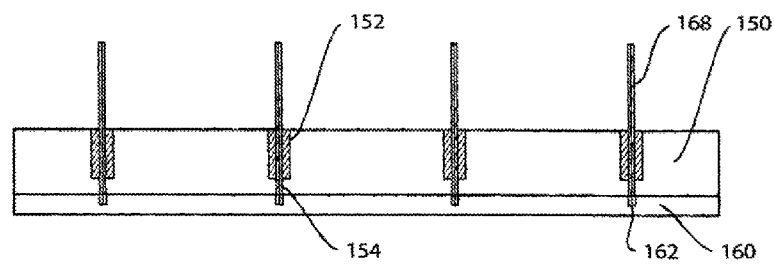
FIG. 8
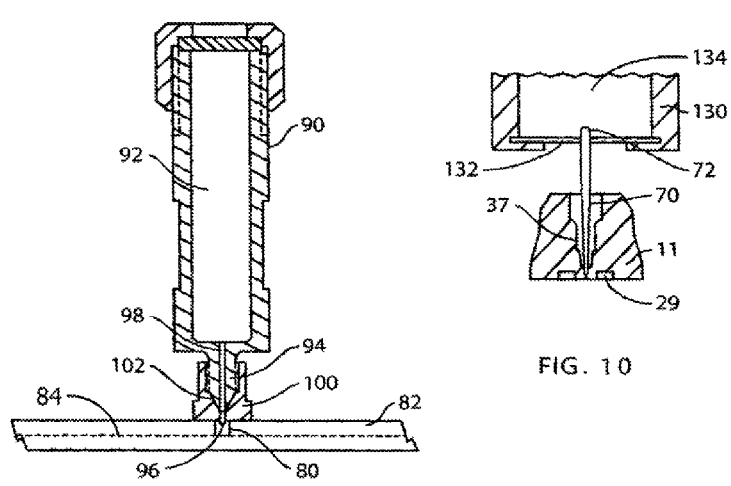
FIG. 9
FIG. 10

MICROMANIFOLD ASSEMBLY

CROSS-REFERENCE TO RELATED APPLICATIONS

This application is a divisional application of and claims priority to prior U.S. patent application Ser. No. 10/405,842, now issued U.S. Pat. No. 7,553,455, originally filed Apr. 2, 2003 and entitled "Micromanifold Assembly" from which benefit is claimed.

STATEMENT OF GOVERNMENT SUPPORT

This invention was made with Government support under Contract No. DE-AC04-94AL85000 awarded by the U.S. Department of Energy to Sandia Corporation. The Government has certain rights to the invention.

FIELD OF THE INVENTION

The present invention relates generally to microfluidic systems and more particularly to structures which facilitate the introduction of fluids into the channels of microfluidic devices.

BACKGROUND OF THE INVENTION

Devices for performing chemical analysis have in recent years become miniaturized. For example, microfluidic devices have been constructed using microelectronic fabrication and micromachining techniques on planar substrates such as glass, silicon or plastic which incorporate a series of interconnected channels or conduits to perform a variety of chemical analyses such as capillary electrophoresis (CE) and high-performance liquid chromatography (HPLC).

Microfluidic substrates have networks that are connected by channels which have mesoscale dimensions, where at least one dimension is usually between 0.1 microns and 500 microns. Such microfluidic substrates may be fabricated using photolithographic techniques similar to those used in the semiconductor industry, and the resulting devices can be used to perform a variety of sophisticated chemical and biological analytical techniques. Microfluidic analytical technology has a number of advantages, including the ability to use very small sample sizes, typically on the order of nanoliters or less. The substrates may be produced at a relatively low cost, and can be formatted to perform numerous specific analytical operations, e.g., protein separations, fluidic mixing, dispensing, valving, reactions, and detections.

Other applications for microfluidic devices include diagnostics involving biomolecules and other analytical techniques such as micro-total analysis systems. Such devices, often referred to in the art as "microchips," also may be fabricated from plastic, with the channels being etched, machined or injection molded into individual substrates. Multiple substrates may be suitably arranged and laminated to construct a microchip of desired function and geometry. In all cases, the channels used to carry out the analyses typically are of capillary scale dimensions.

To fully exploit the technological advances offered by the use of microfluidic devices and to maintain the degree of sensitivity for analytical techniques when processing small volumes, e.g., microliters or less, connectors which introduce and/or withdraw fluids, i.e., liquids and gases, from the device, as well as interconnect microfluidic devices, are a crucial component in the use and performance of the microfluidic device.

A common technique used in the past involves bonding a length of tubing to a port on the microfluidic device with epoxy or other suitable adhesive. Adhesive bonding is unsuitable for many chemical analysis applications because the solvents used attack the adhesive which can lead to channel clogging, detachment of the tubing, and/or contamination of the sample and/or reagents in or delivered to the device. Furthermore, adhesive bonding results in a permanent attachment of the tubing to the microfluidic device which makes it difficult to change components, i.e., either the microfluidic device or the tubing, if necessary. Thus assembly, repair and maintenance of such devices become labor and time intensive, a particularly undesirable feature when the microfluidic device is used for high throughput screening of samples such as in drug discovery.

Other methods involved introducing liquids into an open port on the microfluidic device with the use of an external delivery system such as a micropipette. However, this technique also is undesirable due to the possibility of leaks and/or spills which may lead to contamination. In addition, the fluid is delivered discretely rather than continuously. Moreover, the use of open pipetting techniques does not permit the use of elevated pressure for fluid delivery such as delivered by a pump, thereby further restricting the applicability of the microfluidic device.

Microfluid systems typically include reservoirs or wells that are etched into the substrate and connected directly to fluid channels to provide fluids necessary to perform various analytical, separations, or chemical synthesis functions. However, because of size constraints imposed by the substrate, the reservoirs are necessarily limited in volume. Thus, any operation such as serial operations that consume relatively large volumes of fluid requires that the reservoirs be filled repeatedly, a task which is onerous and prone to error. In certain operations, it can also be desirable to change the composition of the solutions running through the microfluid system, which can also be very difficult when employing a system with small reservoirs disposed in a substrate.

As is apparent, there is a need for a device for introducing large quantities of fluids into a substrate from an external source and which can be advantageously used in a number of assay formats for high-throughput applications.

SUMMARY OF THE INVENTION

The invention is based in part on the development of micromanifold assemblies for connecting external capillaries to the inlet and/or outlet ports of a microfluidic device.

In particular, the invention is based in part on the development of a ferrule/capillary assembly that includes:

a ferrule comprising an elongated member and having a bore traversing from a proximal end to a distal end of the member, wherein the bore has an inner surface and wherein the distal end of the ferrule has a tapered, threaded exterior surface; and a capillary that is positioned within the bore wherein the capillary's outer surface is in direct contact with the bore's inner surface.

In one aspect, the invention is directed to a fluid connector assembly coupling at least one fluid source to at least one port of a substrate that includes:

a manifold comprising one or more channels extending therethrough;

a substrate, having one or more ports on a first surface that is positioned against the manifold, wherein the one or more ports are aligned with the one or more channels of the manifold and wherein the so aligned port(s) and channel(s) are in fluid communication;

means for securing a proximal end of one or more elongated fluid conduits to the one or more channels wherein at least one distal end of the elongated fluid conduits is connected to a fluid source; and means for securing the first surface of the substrate to a first surface of the manifold which is facing the substrate to form a fluid tight seal.

In another aspect, the invention is directed to a fluid connector assembly coupling at least one fluid source to at least one port of a substrate that includes:

a manifold having one or more hollow needles extending therethrough with each needle having a proximal end projecting beyond a first surface of the manifold;

a substrate, having one or more ports on a first surface that is positioned against the manifold, wherein the one or more ports are aligned with the one or more distal ends of the one or more hollow needles in the manifold and wherein the so aligned port(s) and distal end(s) are in fluid communication, and wherein one or more proximal ends of the hollow needle are connected to a fluid source; and means for securing the first surface of the substrate to a second surface of the manifold to form a fluid tight seal.

In a further aspect, the invention is directed to a fluid connector assembly coupling at least one fluid source to at least one port of a substrate that includes:

a manifold having one or more channels extending therethrough, wherein at least one channel defines a threaded or interlocking snap-ring interior cavity securing a ferrule which defines a bore and which has a hollowed member projecting from the bore;

a fluid source which comprises a reservoir comprising a chamber that contains a fluid and an aperture through which the hollowed member is inserted so that the chamber is in fluid communication with the bore of the ferrule;

a substrate, having one or more ports on a first surface that is positioned adjacent the manifold, wherein the one or more ports are aligned with the one or more channels so that aligned port(s) and channel(s) of the manifold are in fluid communication; and means for securing the first surface of the substrate to a first surface of the manifold facing the first surface of the substrate to form a fluid tight seal.

In yet another aspect, the invention is directed to a fluid connector assembly that couples a fluid source to a substrate port that includes:

a port connector or member having a channel extending therethrough with the channel having an opening at a first surface of said port connector member;

a substrate, having a port on a first surface that is positioned adjacent the port connector member, wherein the port is aligned with the opening on the first surface of the port connector member; and a fluid source comprising a container having a chamber storing a fluid sample and having a nozzle with an aperture that is positioned within the channel so that the aperture is in fluid communication with port and the substrate, and wherein the first surface of the port connector member is secured to the first surface of the substrate to form a fluid tight seal.

BRIEF DESCRIPTION OF THE DRAWINGS

FIG. 8 is a cross-sectional view of a micromanifold wherein the capillaries are bonded to the manifold channels;

FIG. 9 is a partial cross-sectional view of a micromanifold with a needle positioned within the channel that is connected to a reservoir; and FIG. 10 is a cross-sectional view of a reservoir mounted in a port connector.

DESCRIPTION OF THE PREFERRED EMBODIMENTS

The invention is directed to techniques for connecting multiple capillaries and/or devices, such as fluid reservoirs, to the microchannels of microscale analytic devices, generally referred to herein as "substrates". The inventive manifold is expected to withstand pressures up to at least about 500 psi. As used herein, the term "microfluidic channel," or "microchannel" is a channel, e.g., sealed enclosed groove, depression, tube, or capillary, which is adapted to handle small volumes of fluid. Typically, the channel has at least one subsection with at least one cross-sectional dimension of between about 0.1 microns and 500 microns, and typically less than 100 microns. As used herein, the term "capillary" refers to a tube with a small internal diameter that typically ranges from 1 micron to 250 microns and an outer diameter that typically ranges from 5 microns to 500 microns. The tubes can be flexible, semi-rigid, or rigid.

Figure 1:
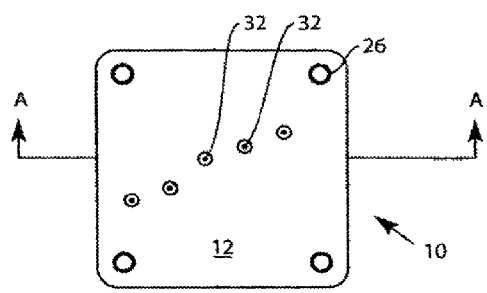
FIG. 1 is the top plan view of a micromanifold assembly.
Figure 2:
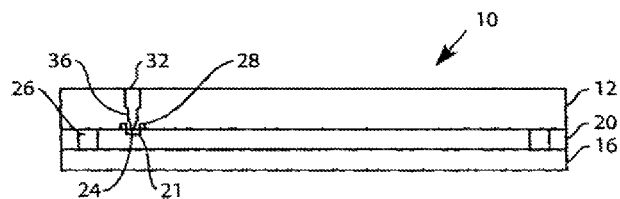
FIG. 2 is the cross-sectional view of the micromanifold assembly of FIG. 1 along the A-A line.

As shown in FIGS. 1 and 2, the micromanifold assembly 10 includes manifold 12 and base plate 16 and substrate 20 that is disposed in between. The manifold preferably is configured as a flat plate. The assembly is secured by screws 26. Other fasteners can be used including bolts that can optionally be spring loaded. Alternative means of non-permanent securing of the assembly include magnetic or vacuum-generated forces, epoxy bonds, or energy-activated devices such as, for example, a solenoid-controlled clamp, or any conventional device which facilitates parts replacement.

Substrate 20 typically has an array of inlet and/or outlet ports on its upper surface facing the lower surface of manifold 12. The inlet and/or outlet ports are connected to an integrated network of microfluidic channels within substrate 20 through via ports, as further described herein. Manifold 12 includes a corresponding array of threaded, tapered channels 36 that traverse the height of the manifold. As shown in FIG. 2, each threaded channel 36 has an upper aperture 32 on the upper surface of manifold 12 and a lower aperture 24 on the lower surface of manifold 12. Concentric with each lower aperture 24 on the underside of manifold 12 is a groove that is fitted with an O-shaped ring 28 that provides a fluid-tight seal between substrate 20 and manifold 12. The O-shaped rings can be made of any suitable deformable material such as natural rubber or silicone.

The threaded channels 36 are preferably arranged within manifold 12 so that the upper apertures 32 (as shown in FIG. 1) are sufficiently spaced apart for easy access. Preferably, the manifold is made of a material such as polyether ether ketone (PEEK), high density polyethylene, polytetrafluoroethylene, or other hard polymer.

As shown in FIG. 2, at least one of the threaded channels 36 of manifold 12 is aligned with one of the ports 21 of substrate 20. In one embodiment, a dedicated manifold can be designed with a specific arrangement of threaded channels 36 that matches the array of ports located on the top surface of a particular substrate such that all the ports are aligned with corresponding lower apertures 24 of threaded channels 36. In this fashion, different substrates can be identified by their different port patterns. Using dedicated manifolds facilitates matching a manifold with the correct substrate. Alternatively, the manifold can have different sets of arrangements of threaded channels to accommodate different substrates. Standard port or hole spacing reduces the need for custom manifold designs.

Figure 3:
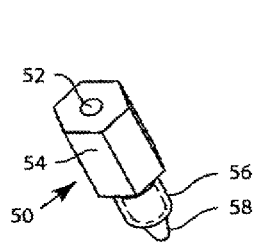
FIGS. 3 and 4 are perspective and cross-sectional views of a ferrule.
Figure 4:
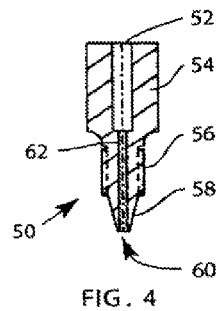

FIGS. 3 and 4 show a threaded ferrule 50 that is designed to be screwed into a threaded, tapered channel 36 as shown in FIG. 2. The ferrule includes an upper handle 54, an externally threaded middle portion 56, and a lower tapered end 58. To facilitate handling, the exterior surface of handle 54 has a polygonal, e.g., hexagonal, contour. Ferrule 50 also has internal bore 62 that runs the length of the ferrule from inlet 52 to outlet 60. Preferably, as shown in FIG. 4, inlet bore 52 is wider than internal bore 62 and tapered end 58 of the ferrule. In this fashion, a capillary tube can be readily maneuvered into the bore through the upper handle. The wall of the bore at the tapered end collapses against the capillary tube as compressive forces are created when the ferrule is screwed into the thread tapered channel 36 of manifold 12. This effectively prevents the capillary tube from extruding during high pressure operations and forms a fluid seal. Preferably each ferrule is constructed as a single, integral piece with no mating sleeve. It can be fabricated by machining a single block of deformable material such as PEEK.

When positioning the capillary, one end of the capillary is preferably inserted into bore 62 of ferrule 50 until the end of the capillary tube reaches outlet 60 of the ferrule or slightly beyond outlet 60. The other end of the capillary is connected, for instance, to a source of reagent or solvent, or a disposable chamber, as the case may be. In this fashion, one end of the capillary will be adjacent to or inside an inlet/outlet port 21 of substrate 20 as illustrated in FIG. 2.

Figure 5:
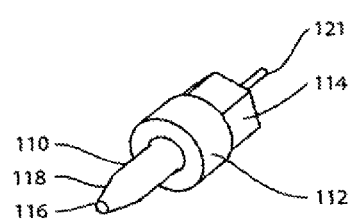
FIGS. 5 and 6 are perspective and cross-sectional views of a ferrule fitted with a capillary tube.
Figure 6:
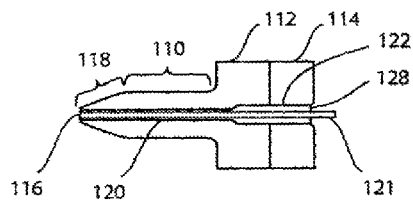

FIGS. 5 and 6 show another embodiment of a threaded, one piece ferrule. The ferrule includes an adapter body 112 having an hexagonal nut 114 on one side and elongated members 110, 118 on the other side. Standard dimensioned threads (not shown) are made on the surface of elongated member 110 by conventional machining techniques. End portion 118 of the elongated member is tapered. The ferrule has internal bore 120, 122 that runs the length of the ferrule from inlet 128 to outlet 116. Preferably, as shown in FIG. 6, the proximal portion 122 of the bore is broader to facilitate insertion of tube 121 into the narrower distal portion 120 of the bore. The wall of the bore at the tapered end will collapse against the tube as compressive forces are created as the ferrule is screwed into the threaded tapered channel 36 of manifold 12. This effectively prevents the capillary tube from extruding during high pressure operations and forms a fluid seal.

As shown in FIG. 6, the tube 121, which is preferably a capillary, fits inside internal bore 120 and comes in direct contact with the internal bore surface. No mating sleeve that is positioned around the outer surface of tube 121 is needed.

Each ferrule is machined from a block of material to fabricate a single, integral piece ferrule. The bore is formed using conventional drills and threads are machined preferably on the exterior of the non-taper portion 110 of the elongated member. When using the ferrule, no flange is needed. In addition, a mating sleeve is not needed since the bore will collapse against the tube under compressive force. By "mating sleeve" it is meant an extra tube that is inserted into the bore of the ferrule before the capillary tube that will be transferring a fluid of interest is inserted through the bore of the mating sleeve. Mating sleeves having an outer diameter that matches the inner diameter of prior art ferrules are used quite often but are not needed with the inventive ferrule. Because the inventive "one-piece" ferrules are fabricated by machining, i.e., they are not made by molding. Therefore, a wide variety of materials can be used, including plastics, ceramics, and metals, for example, depending on the expected operating conditions, such as, temperature, pressure, and the type of fluids used. The ferrules are reusable and can be finger-tightened to provide a seal that can withstand a minimum pressure of 5,000 psi.

In a preferred embodiment, ferrule features are maintained at minimum dimensions that still provide for the requisite sealing torque applied via typical thumb-and-forefinger tightening, without the use of torque-enhancing tools.

The ferrule is particularly suited for high pressure operations for connect capillary tube connections. In this regard, referring to the ferrule shown in FIG. 6, the diameter of the distal portion 120 of the bore is typically 0.0145 in. (0.368 mm) to 0.015 in. (0.38 mm) and the diameter of the proximal portion 122 of the bore is typically 0.018 in. (0.46 mm) to 0.020 in (0.51 mm). In practice, after a substrate has been aligned and secured between the base plate and the manifold, one or more ferrule(s) each with a capillary tube is screwed into the appropriate threaded tapered channel of the manifold. As the ferrule is screwed on, the compressive pressure causes the internal bore of the ferrule to collapse against the capillary tube thereby gripping the capillary. Once the ferrules are in place, fluid(s) can be transferred into and/or out of the substrate through the capillaries.

Figure 7:
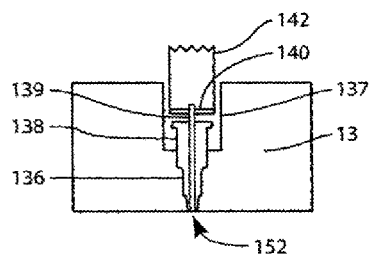
FIG. 7 is a partial cross-sectional view of a micromanifold with a threaded channel with a ferrule therein that is connecting a reservoir.

FIG. 7 illustrates another technique for connecting a vial of fluid to a substrate. In this embodiment, manifold 13 has a threaded, tapered channel 136 traversing its height. The lower surface of manifold 13 is in contact with a substrate (not shown) so that an inlet or outlet on the substrate surface is in fluid communication with the lower aperture 152 on the lower surface of manifold 13. The tapered channel 136 accommodates a ferrule 138 which has been modified to include a needle 139 projecting from its proximal end. The ferrule can be that shown in FIGS. 3 and 4 but preferably has a shortened hexagonal shaped handle so that the entire ferrule fits within the channel. A vial 142, which has a chamber with an aperture that is covered by septum 140, is positioned so that the proximal end of the needle 139 pierces or perforates through septum 140. Preferably, the aperture is elongated and dimensioned to fit in the upper section 137 of the channel. In this configuration, the walls of the upper part of the channel provide lateral support for the vial.

FIG. 8 illustrates a micromanifold assembly where the capillaries are bonded to the manifold channels so that ferrules are not needed. As shown, the assembly includes manifold 150 having a plurality of channels that traverse the height of the manifold. Each channel preferably has a wider upper portion 152 and a narrower lower portion 154 which has a lower aperture. The contour and cross-sectional dimensions of the lower portion 154 should preferably match that of the capillary so that a capillary tube fits snugly therein. Substrate 160, e.g., microchip, has a plurality of outlet and/or inlet ports 162 at its upper surface. The substrate is positioned immediately against the lower surface of the manifold so that the lower apertures of the channels are aligned with the ports of the substrate. The manifold and substrate can be joined together by adhesive bonding and/or mechanical techniques described above. Once the capillaries 168 are inserted into the channels of the manifold with the tips of the capillaries preferably being within the ports of the substrate as shown, an adhesive, e.g., epoxy, can be poured into the channel. When the adhesive cures, the capillaries are permanently secured.

FIG. 9 illustrates a technique for connecting a reservoir 90 to a via port 80 of substrate 82. The via port is in fluid communication with microchannels 84 within the substrate. The reservoir 90 can be any container having a chamber 92 filled with a liquid that is to be supplied to the substrate. Alternatively, the chamber can be used to store material, e.g., waste solvent, from the substrate as well. The reservoir includes a nozzle 94 with an aperture 96 through which a fluid is delivered or received. The nozzle 94 includes a channel 98 that is in communication with chamber 92. The nozzle 94 has an opening that may be capped or covered with a septum.

As is illustrated, a port connector 100 is mounted on the surface of substrate 82. Particularly for higher pressure applications or single port applications, the port connector 100 can be attached to the surface of the substrate 82 by conventional means such as, for example, with adhesives, e.g., epoxy, and/or mechanical fasteners. (Adhesive bonding is effective to withstand operation pressures of over 10,000 psi.) The port connector 100 is preferably an elongated member that has an interior cavity 102 which is contoured to match the exterior contour of nozzle 94. The port connector is mounted so that the distal end of aperture 96 is concentric with the inlet/outlet port 80 of substrate 82. In a preferred embodiment, port connector 100 has a threaded cavity structure configured in the same way as the modified threaded channel of the manifold as shown in FIG. 10. In this case, the exterior contour of nozzle 94 is designed similarly to that of ferrule 50 as illustrated in FIGS. 3 and 4. In use, open or film-covered nozzle 94 of reservoir 90 is inserted into the tapered cavity 102 of port connector 100. The exterior surface of cavity 102 and the corresponding mating exterior surface of nozzle 94 can also be threaded or provided with an interlocking snap-ring mechanism to provide improved pressure-tight seal.

Finally, FIG. 10 illustrates another technique for supplying fluids to or removing fluids from a substrate. The threaded, tapered channel 37 of manifold 11 includes a hollow needle or shaft 70 that has a proximal end 72 which projects above the plane of the upper surface of manifold 11 and a distal end 74 that preferably extends to the lower surface of manifold 11 so that the needle would be adjacent the inlet or outlet of a substrate (not shown) to which manifold 11 is in contact. Needle 70 can be any suitably elongated structure with an internal passageway through which fluid flows. The needle is preferably made of a sufficiently rigid material such as stainless steel so that its proximal end 72 will pierce through film or septum 132 that covers the aperture of vial or reservoir 130 or other storage container. In this fashion, the inlet or outlet of the substrate is in fluid communication with chamber 134 of vial 130. A groove which is concentric with the lower aperture is fitted with an O-shaped ring 29. The needle can also be a short fragment of capillary. Alternatively, rather than inserting needle 70 into a threaded, tapered channel 37 in manifold 11, the needle can be perforated through a solid portion of the manifold.

Suitable substrates for the present invention can be any substantially planar microfluidic member that has an integrated network of microfluidic channels disposed therein. The particular design or configuration of the internal structure of the substrate is not critical. Such substrates are also referred as microfluidic wafers or chips. The substrate is preferably fabricated from glass, quartz, silicon or plastic by conventional techniques including LIGA (an acronym for the German for lithography, electroplating, and molding), deep x-ray lithography, silicon surface micromachining and lithography, electric discharge machining, and direct laser additive fabrication. In addition, commercially available substrates can be modified with appropriate dimensioned inlet and/or outlet ports as further described herein. The substrate may include reaction cells, reservoirs, and other structures that are interconnected by a network of microchannels and a series of micropumps. Such substrates are further described in U.S. Pat. No. 5,846,396 to Zanzucchi, et al. which is incorporated herein.

The substrate includes a plurality of inlet and/or outlet ports provided for fluid communication with microchannels within the substrate. For example, inlet ports can be employed to introduce reagents and cleaning solvents into the substrate while outlet ports can be employed to remove products and solvents from the system.

Conventional mechanical pumps can be employed to transfer fluids from a remote source through capillaries that are attached to the ferrules and eventually into the substrates. For high pressure application, a preferred method employs a high pressure hydraulic system that has no moving parts for converting electric potential to hydraulic force and for manipulating fluids which are described in U.S. Pat. Nos. 6,013,164 to Paul, et al., 6,019,882 to Paul, et al., 6,224,728 to Obomy, et al. and 6,277,257 and 6,290,909 both to Paul, et al. which are incorporated herein by reference.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A fluid connector assembly coupling at least one fluid source to at least one port of a microfluidic device comprising:
    at least one fluid source comprising a chamber, a fluid contained within the chamber and an opening aperture covered by a septum;
    a manifold having one or more channels extending therethrough and a hollow needle bonded into each of the one or more channels with each needle having a distal end projecting beyond a bottom surface of the manifold;
    a microfluidic device comprising an integrated network of microchannels and one or more inlet and outlet ports formed into a top surface of a substrate that is positioned adjacent to the manifold bottom surface, wherein each of the one or more inlet and outlet ports is in fluid communication with at least one of the one or more microchannels, wherein the one or more inlet and outlet ports are each aligned with the distal end of one of the one or more hollow needles in the manifold, wherein the so aligned inlet and outlet ports and distal ends are in fluid communication; and
    means for securing the top surface of the microfluidic device to the bottom surface of the manifold to form a fluid tight seal therebetween, wherein the proximal end of at least one of the hollow needles pierces the septum of the at least one fluid source so that fluid contained within is brought into fluid communication with at least one of the inlet and outlet ports.

2. The fluid connector assembly of claim 1 wherein the fluid source is a reservoir.

3. The fluid connector assembly of claim 1 further comprising a compression plate that is positioned adjacent the microfluidic device and that is secured to the microfluidic device with sufficient force so that a fluid tight seal is created between the bottom surface of the manifold and the top surface of the microfluidic device.

4. The fluid connector assembly of claim 3 wherein the microfluidic device is held in position between the manifold and compression plate by non-permanent securing means.

5. The fluid connector assembly of claim 3 wherein the microfluidic device is held in position between the manifold and the compression plate by one or more securing devices that is selected from the group consisting of a bolt, a spring loaded bolt, a screw, a spring loaded screw, a clamp, an electrically activated solenoid, and combinations thereof.

6. The fluid connector assembly of claim 3 wherein the microfluidic device is held in position between the manifold and the compression plate by a power-generating device that generates a compressive force.

7. The fluid connector assembly of claim 1 wherein the manifold bottom surface further defines one or more channel outlets where distal ends of the one or more hollow needles exit the manifold, and wherein each outlet defines an annular groove surrounding the outlet that contains a seal material.

8. The fluid connector assembly of claim 7 wherein the seal material is an O-shaped ring comprising a plastic or silicone rubber.

\* \* \* \* \*